(12) United States Patent
Pancheco et al.

(10) Patent No.: US 9,687,284 B2
(45) Date of Patent: Jun. 27, 2017

(54) LOCKING PEG WITH EXTENDED THREAD

(71) Applicants: Fernando Pancheco, Zürich (CH); Martin Knape, Freiburg (DE); Egon Hermann, Denzlingen (DE); Kevin Soldan, Solothurn (CH)

(72) Inventors: Fernando Pancheco, Zürich (CH); Martin Knape, Freiburg (DE); Egon Hermann, Denzlingen (DE); Kevin Soldan, Solothurn (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 242 days.

(21) Appl. No.: 14/156,657

(22) Filed: Jan. 16, 2014

(65) Prior Publication Data

US 2014/0228894 A1    Aug. 14, 2014

Related U.S. Application Data

(60) Provisional application No. 61/764,173, filed on Feb. 13, 2013.

(51) Int. Cl.
| | |
|---|---|
| *A61B 17/86* | (2006.01) |
| *A61B 17/88* | (2006.01) |
| *A61B 17/80* | (2006.01) |

(52) U.S. Cl.
CPC .......... *A61B 17/861* (2013.01); *A61B 17/863* (2013.01); *A61B 17/866* (2013.01);
(Continued)

(58) Field of Classification Search
CPC .............. A61B 17/8625; A61B 17/863; A61B 2017/8655; A61B 17/8057
See application file for complete search history.

(56) References Cited

U.S. PATENT DOCUMENTS

| | | | |
|---|---|---|---|
| 4,463,753 | A | 8/1984 | Gustilo |
| 4,760,843 | A | 8/1988 | Fischer et al. |
| | | (Continued) | |

FOREIGN PATENT DOCUMENTS

| | | |
|---|---|---|
| EP | 1649819 A1 | 4/2006 |
| EP | 1690509 A1 | 8/2006 |
| | (Continued) | |

OTHER PUBLICATIONS

Extended European Search Report for Application No. 14000469.8 dated May 30, 2014.
(Continued)

*Primary Examiner* — David Bates
*Assistant Examiner* — Olivia C Chang
(74) *Attorney, Agent, or Firm* — Lerner, David, Littenberg, Krumholz & Mentlik, LLP (57) ABSTRACT

A locking peg includes a head and a shaft. The head is at the proximal end of the locking peg, and a shaft extends distally from the head to a distal end of the locking peg. The shaft has a threaded proximal portion and an unthreaded distal portion. A length of the unthreaded distal portion of the shaft is greater than a length of the threaded proximal portion of the shaft. When the locking peg is inserted into a bone through a bone plate, the threaded proximal portion of the shaft extends into the bone. This extended threading provides additional axial force to help explant the locking peg during removal of the locking peg.

5 Claims, 7 Drawing Sheets

(52) U.S. Cl.
CPC .......... *A61B 17/8875* (2013.01); *A61B 17/80* (2013.01); *A61B 17/8605* (2013.01); *A61B 2017/8655* (2013.01); *Y10T 29/49995* (2015.01)

(56) References Cited

U.S. PATENT DOCUMENTS

| | | | |
|---|---|---|---|
| 5,360,448 | A | 11/1994 | Thramann |
| 5,360,452 | A | 11/1994 | Engelhardt et al. |
| 5,375,956 | A | 12/1994 | Pennig |
| 5,759,184 | A | 6/1998 | Santangelo |
| 5,871,504 | A | 2/1999 | Eaton et al. |
| 5,954,722 | A | 9/1999 | Bono |
| 5,968,047 | A | 10/1999 | Reed |
| 6,019,762 | A | 2/2000 | Cole |
| 6,129,730 | A * | 10/2000 | Bono ................. A61B 17/8047 606/271 |
| 6,162,234 | A | 12/2000 | Freedland et al. |
| 6,306,140 | B1 | 10/2001 | Siddiqui |
| 6,699,248 | B2 | 3/2004 | Jackson |
| 6,808,526 | B1 | 10/2004 | Magerl et al. |
| 6,955,677 | B2 | 10/2005 | Dahners |
| 7,491,236 | B2 | 2/2009 | Cragg et al. |
| 7,637,928 | B2 | 12/2009 | Fernandez |
| 7,905,909 | B2 | 3/2011 | Orbay et al. |
| 7,967,851 | B2 | 6/2011 | Bickley et al. |
| 8,080,044 | B2 | 12/2011 | Biedermann et al. |
| 8,496,694 | B2 | 7/2013 | Hashmi et al. |
| 2004/0127909 | A1 | 7/2004 | Morgan |
| 2005/0131413 | A1* | 6/2005 | O'Driscoll ......... A61B 17/8052 606/286 |
| 2006/0149265 | A1* | 7/2006 | James ................ A61B 17/8057 606/281 |
| 2006/0200151 | A1* | 9/2006 | Ducharme .......... A61B 17/863 606/305 |
| 2006/0276788 | A1 | 12/2006 | Berry et al. |
| 2007/0009340 | A1* | 1/2007 | Van Cor ................. F16B 35/06 411/426 |
| 2007/0088360 | A1 | 4/2007 | Orbay et al. |
| 2007/0093837 | A1* | 4/2007 | Bohrmann ......... A61B 17/8605 606/326 |
| 2008/0140130 | A1 | 6/2008 | Chan et al. |
| 2008/0188899 | A1 | 8/2008 | Bottlang et al. |
| 2008/0234675 | A1 | 9/2008 | Ohrnell et al. |
| 2008/0234763 | A1 | 9/2008 | Patterson et al. |
| 2008/0306555 | A1 | 12/2008 | Patterson et al. |
| 2009/0062868 | A1 | 3/2009 | Casutt |
| 2009/0105768 | A1 | 4/2009 | Cragg et al. |
| 2009/0125028 | A1* | 5/2009 | Teisen .................... A61B 17/68 606/63 |
| 2009/0182385 | A1 | 7/2009 | Smith |
| 2009/0210067 | A1 | 8/2009 | Meridew |
| 2009/0240291 | A1 | 9/2009 | Gorek |
| 2009/0275993 | A1 | 11/2009 | Phan et al. |
| 2010/0076496 | A1 | 3/2010 | Fernandez |
| 2010/0094356 | A1 | 4/2010 | Varela et al. |
| 2010/0131012 | A1 | 5/2010 | Ralph et al. |
| 2010/0174323 | A1 | 7/2010 | Fourcault et al. |
| 2011/0118795 | A1 | 5/2011 | Hashmi et al. |
| 2011/0276095 | A1 | 11/2011 | Bar et al. |
| 2011/0313473 | A1 | 12/2011 | Prandi et al. |
| 2012/0232599 | A1* | 9/2012 | Schoenly ........... A61B 17/8635 606/315 |

FOREIGN PATENT DOCUMENTS

| | | |
|---|---|---|
| IE | 59317 B1 | 2/1994 |
| WO | 2007095447 A1 | 8/2007 |
| WO | 2008115318 A1 | 9/2008 |
| WO | 2009023666 A2 | 2/2009 |
| WO | 2011062896 A1 | 5/2011 |
| WO | 2011154891 A2 | 12/2011 |

OTHER PUBLICATIONS

European Examination for Application No. 14000469.8 dated Jul. 7, 2015.

* cited by examiner

LOCKING PEG WITH EXTENDED THREAD

CROSS-REFERENCE TO RELATED APPLICATIONS

The present application claims the benefit of the filing date of U.S. Provisional Patent Application No. 61/764,173 filed Feb. 13, 2013, the disclosure of which is hereby incorporated herein by reference.

BACKGROUND OF THE INVENTION

The present invention relates to bone plates and the manner in which they are connected to bone, and more particularly, to locking pegs with extended threads to assist in removing the pegs from bone.

Figure 1:
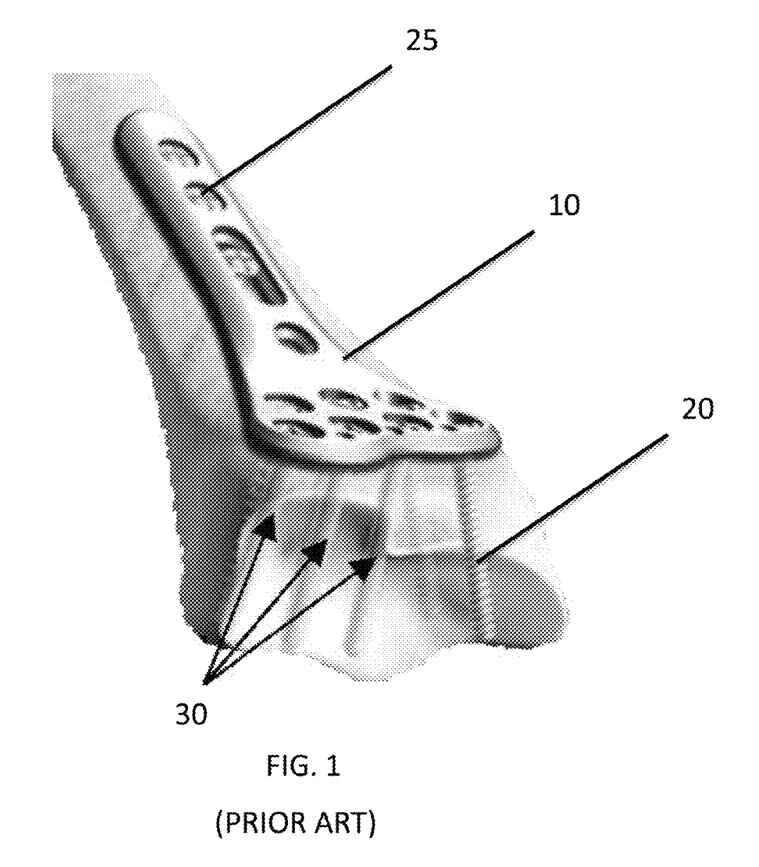
FIG. 1 is a perspective partial phantom view of a bone plate implanted onto a bone according to the prior art.

FIG. 1 illustrates a prior art bone plate fixation system including a bone plate 10, non-locking bone screws 20, locking screws 25, and locking pegs 30. Traditional bone screws 20, locking screws 25, and locking pegs 30 are used to fix bone or at least partially connect plates to bone. Unlike traditional bone screws 20, the shafts of locking pegs 30 generally are unthreaded. Locking pegs 30 may be used, for example, in the distal portion of distal radius plates, as illustrated in FIG. 1. The use of multiple non-parallel locking pegs 30 may provide enough local bone-to-plate fixation such that a thread on the shaft of the locking peg 30 is not necessary.

Among other benefits, locking pegs 30 may be inserted quickly because they may be pushed through a pilot hole in the bone without requiring screwing the shaft into the bone. This substantially reduces the time required to insert the locking peg, such that the locking peg need only be pushed into the pilot hole and screwed a few revolutions to activate the locking mechanism between a threaded head of the locking peg and a threaded hole of the bone plate. Furthermore, because locking pegs 30 have unthreaded shafts, the locking pegs have fewer sharp edges than traditional bone screws 20 and pose less of a risk for damage to tissues surrounding the bone, such as the radial cartilage in the wrist joint. Thus, locking pegs 30 may be especially useful when it is desired to place the locking peg 30 very close to a joint surface.

Figure 2A:
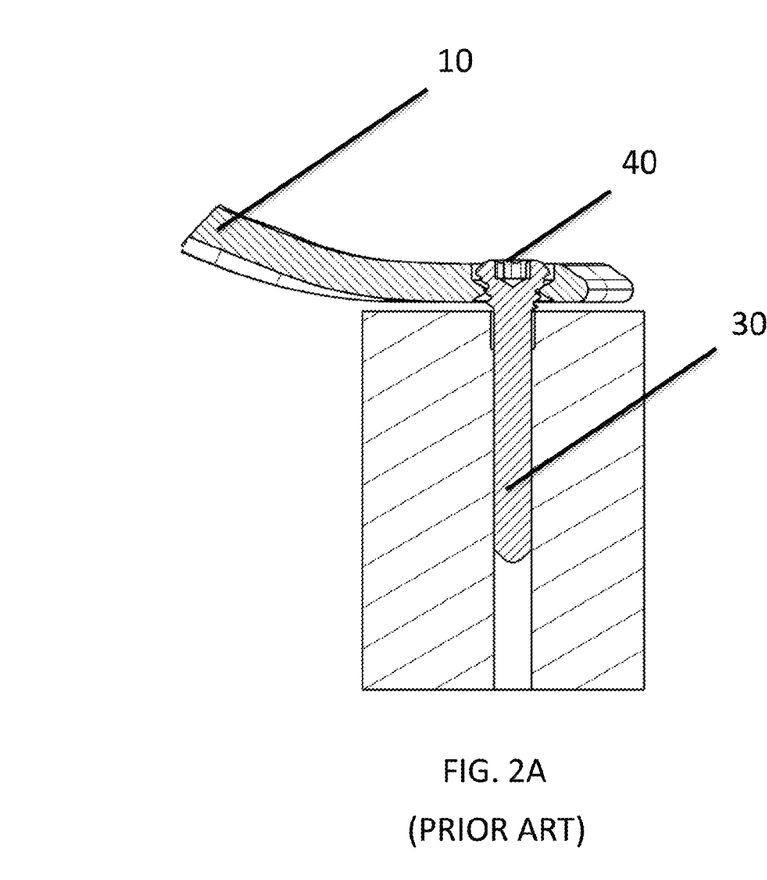
FIGS. 2A-B are sectional side view of a locking peg according to the prior art being removed from a bone and bone plate.
Figure 2B:
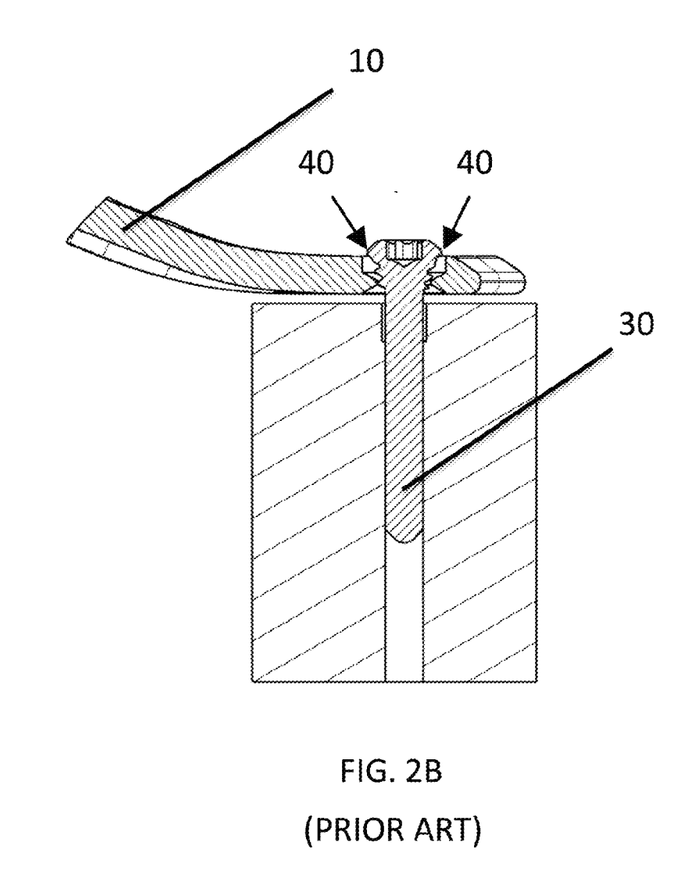

FIGS. 2A-B illustrate steps for explantation (i.e., removal) of locking pegs 30 according to the prior art. Explantation of locking pegs 30 is generally more difficult than explantation of traditional bone screws 20. Because locking pegs 30 have no threading on the shaft, counterclockwise rotation of the locking peg 30 will only disengage the screw head 40 from the bone plate 10. Additional rotation will not provide additional axial force to extract the locking peg 30, as the unthreaded shaft will simply rotate within the bone hole without any translation. Instead, the locking peg 30 must be grasped at the head 40, as illustrated in FIG. 2B, and pulled out of the bone. However, unscrewing the head 40 of the traditional locking peg 30 generally only raises the locking peg 30 by a small amount. Depending on the design of the particular hole in the bone plate 10, it often is difficult to grasp the head 40 of the locking peg 30 with forceps or other devices because the head 40 only protrudes a small distance above the bone plate 10. As a result, surgeons often resort to pulling the locking peg 30 out of the bone by pulling on the bone plate 10. Surgeons may even resort to making an incision in tissue opposite the side of the head 40 of the locking peg 30 to push the locking peg 30 up out of the bone plate 10. Each of these approaches carries risks to the patient.

Therefore, there exists a need for locking pegs that retain the benefits of traditional locking pegs while mitigating issues of difficult removal from the bone.

BRIEF SUMMARY OF THE INVENTION

In one embodiment of the invention, a locking peg includes a head at a proximal end of the locking peg and a shaft extending distally from the head to a distal end of the locking peg. The shaft has a threaded proximal portion and an unthreaded distal portion. The length of the unthreaded distal portion of the shaft is preferably greater than the length of the threaded proximal portion of the shaft. When the locking peg is inserted through a bone plate and into a bone, the threaded proximal portion of the shaft preferably extends approximately 2 to approximately 6 thread revolutions into the bone, more preferably approximately 3 to approximately 5 thread revolutions into the bone, or most preferably approximately 4 thread revolutions into the bone. The threaded proximal portion of the shaft may have double-lead threading. The threaded proximal portion of the shaft may have at least one cutting flute positioned at a distal end of the threaded proximal portion of the shaft.

In another embodiment of the invention, a method of implanting a locking peg includes positioning a bone plate on a bone and creating a pilot hole in the bone. The method also includes inserting an unthreaded distal portion of the shaft of the locking peg into the pilot hole, and rotating the locking peg such that a threaded proximal portion of the locking peg shaft engages the bone. Rotation is continued such that the threaded proximal portion of the locking peg shaft advances further into the bone prior to a threaded head of the locking peg engaging threading in the hold of the bone plate. The locking peg is further rotated until a threaded head of the locking peg engages threading in the hole of the bone plate.

In a further embodiment of the invention, a method of explanting a locking peg includes unscrewing the locking peg that has previously been inserted through a hole of a bone plate and into a bone on which the bone plate is positioned. Unscrewing is continued until a threaded portion of a head of the locking peg no longer engages a threaded portion of the hole of the bone plate. The locking peg is further unscrewed such that a threaded proximal portion of a shaft of the locking peg disengages from the bone. The step of further unscrewing causes the head of the locking peg to travel away from the bone plate. The head of the locking peg is then grasped and the locking peg is removed from the bone. During the step of further unscrewing the locking peg, an unthreaded distal portion of the shaft of the locking peg remains in the bone. Prior to unscrewing the locking peg from the bone, the threaded proximal portion of the shaft may extend between approximately 2 and approximately 6 thread revolutions into the bone.

In another embodiment of the invention, a method of manufacturing a locking peg includes creating one single lead thread extending from a head of the locking peg to a proximal portion of a shaft of the locking peg. Then, a second thread is created between the previously created single lead thread on the proximal portion of the shaft such that the proximal portion of the shaft has a double lead thread. Finally, at least one cutting flute is milled at the distal end of the double lead thread on the proximal portion of the shaft of the locking peg. The double lead thread may preferably extend distally beyond the head between approximately 2 and approximately 6 thread revolutions. More preferably, the double lead thread may extend distally beyond the head between approximately 3 and approximately 5 thread revolutions. Most preferably, the double lead thread may extend distally beyond the head between approximately 4 thread revolutions.

DETAILED DESCRIPTION

As used herein, the term "proximal" means closer to a user of the described devices and methods, such as a surgeon, while the term "distal" means farther away from the user. In the drawings, like numbers refer to similar or identical parts. When values for structures or characteristics of devices are provided, those values are merely illustrative, unless otherwise stated, and those values may be altered without departing from the scope of the invention. When ranges of values are provided, it should be understood that all values within the provided range are included, as well as all ranges within the range provided. For example, a range of 2 to 8 includes the values of 3 and 4, as well as the ranges of 4 to 7 and 3 to 5.

Figure 3A:
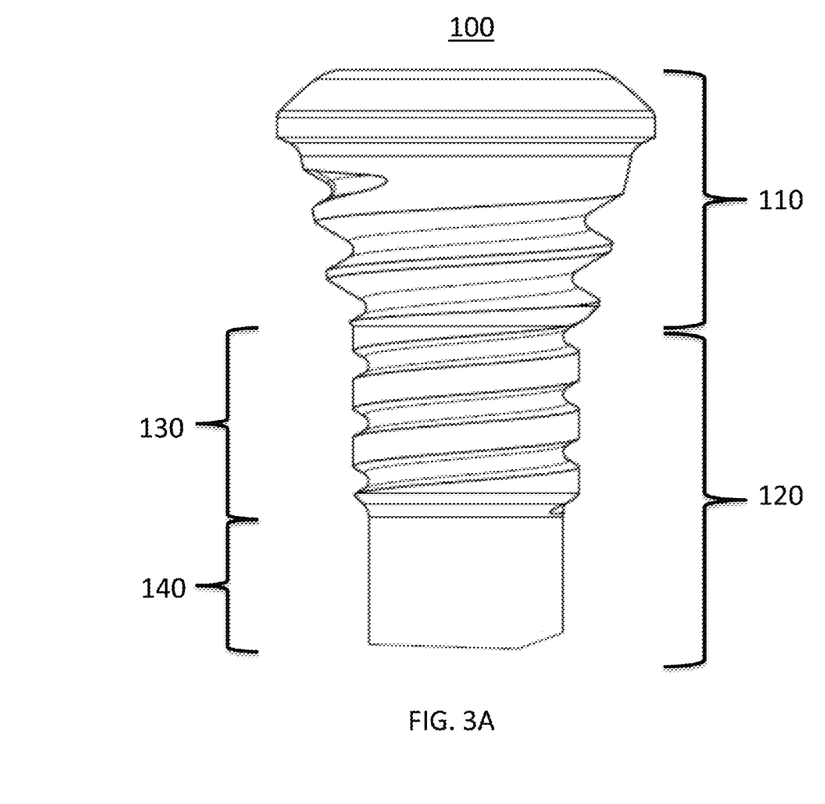
FIG. 3A is a side plan view of a locking peg according to an embodiment of the invention shown after a first step of manufacturing.
Figure 3B:
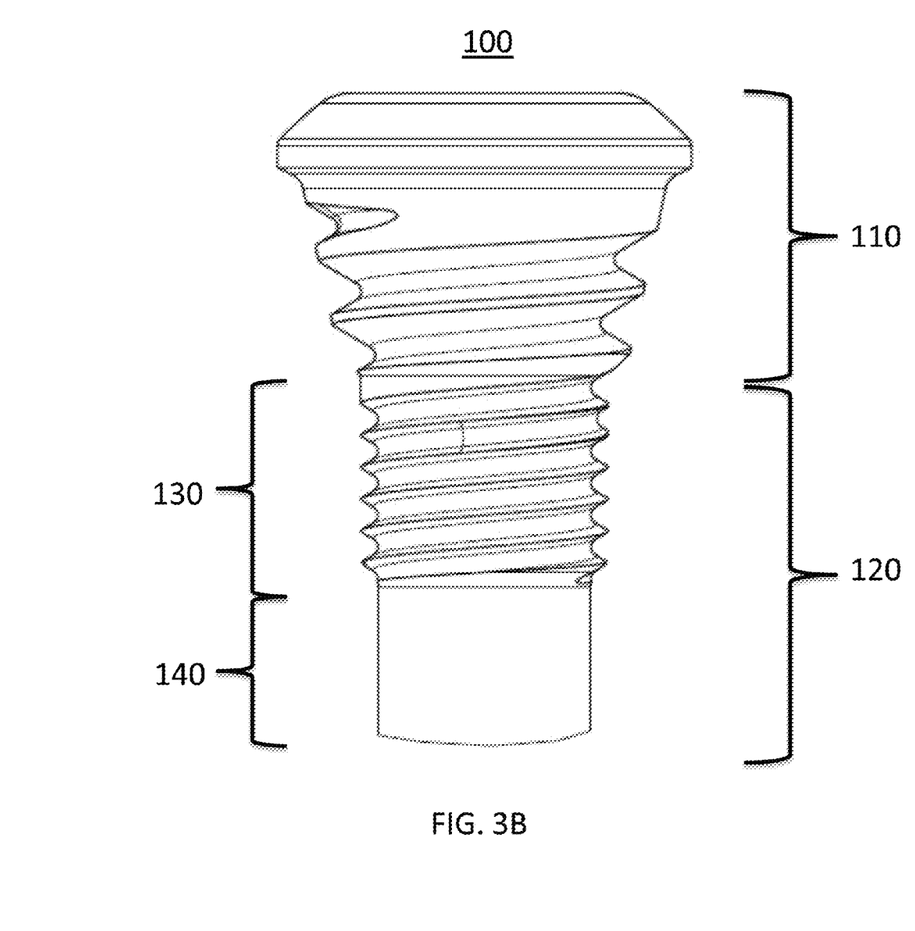
FIG. 3B is a side plan view of the locking peg of FIG. 3A after a second step of manufacturing.
Figure 3C:
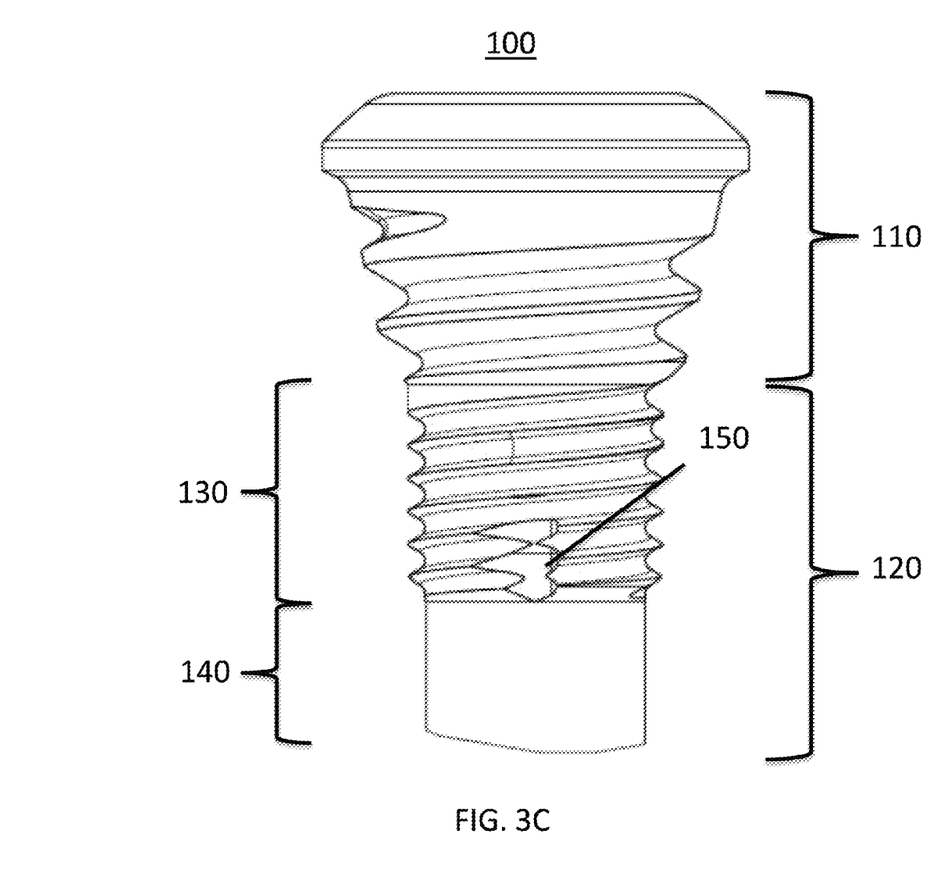
FIG. 3C is a side plan view of the locking peg of FIG. 3A after a third step of manufacturing.

Referring to FIGS. 3A-C, a locking peg 100 is shown according to an embodiment of the invention during different stages of manufacture. As seen in FIGS. 3A-C, locking peg 100 generally includes a head 110 and a shaft 120. The shaft 120 generally includes a proximal portion 130 and a distal portion 140. Like traditional locking pegs, the head 110 of locking peg 100 includes a locking thread configured to mate with complementary threading of a locking hole in a bone plate 10. Unlike tradition locking pegs, however, the locking peg 100 includes threading that extends from the head 110 to the proximal portion 130 of shaft 120. The relationship between the locking threads and the extended threads are discussed in greater detail below. This extended threading provides additional axial force when unscrewing the locking peg 100 out of the bone and a locking hole in the bone plate 10, described in further detail below. In one embodiment, three steps may be performed to create the locking peg 100 with extended threading.

First, as shown in FIG. 3A, as the locking thread of the head 110 is created, the process continues down a portion of the shaft 120, such that a locking thread exists on a proximal portion 130 of the shaft 120. The distal portion 140 of the shaft 120 remains unthreaded.

Second, an additional thread is then added to the locking thread on the proximal portion 130 of the shaft 120 between the previously created thread, such that the proximal portion 130 of the shaft 120 has a double thread, as shown in FIG. 3B. Preferably, the magnitude of the lead on the proximal portion 130 of the shaft 120 is preserved, while the magnitude of the pitch is halved by virtue of the additional thread. This configuration helps ensure that the locking thread on the head 110 and the double thread on the proximal portion 130 of the shaft 120 advance the same distance per revolution of the locking peg 100. One advantage of this configuration is that upon threading the locking peg 100, it moves through the plate and the bone at the same speed, such that the plate and bone do not move relative to one another. If the thread on the proximal portion 130 of the shaft 120 had a greater lead than the thread of the head 110, the plate would be compressed onto the bone during insertion. On the other hand, if the thread on the proximal portion 130 of the shaft 120 had a lead less than the thread of the head 110, the plate would be displaced away from the bone during insertion. In one non-limiting example, the lead and pitch of the locking thread on the head 110 is approximately 0.6 mm. In that example, the lead of the double thread is still approximately 0.6 mm while the pitch of the double thread is approximately 0.3 mm. Each revolution of the locking peg 100 would then advance the locking peg by approximately 0.6 mm. These values are merely illustrative, and may be altered as desired and known by one of skill in the art.

Third, as shown in FIG. 3C, cutting flutes 150 may be created, for example by milling, near the distal end of the proximal portion 130 of the shaft 120. In one embodiment, three cutting flutes 150 are added to the distal end of the proximal portion 130 of the shaft 120 and are generally equally spaced around the circumference of the locking peg 100. The cutting flutes 150 may help the locking peg 100 cut into the bone more effectively. Other features, such as a sharp thread angle, may also help the extended thread cut into bone. A sharp thread angle may be created, for example, through the process described in relation to FIG. 3B.

Figure 4A:
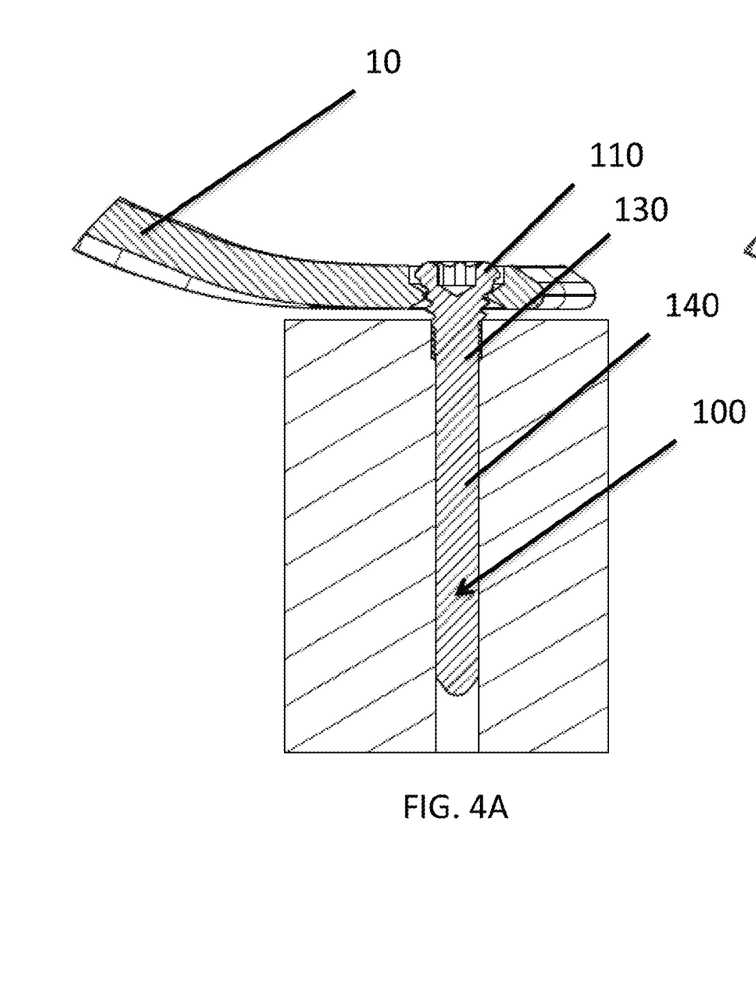
FIGS. 4A-C illustrate sectional side views of a locking peg according to an embodiment of the invention being removed from a bone and bone plate.

As illustrated in FIG. 4A, during use, the locking peg 100 is inserted through a locking hole of a bone plate 10 and through the bone in a generally similar method as would be expected for a traditional locking peg 30. The main difference in inserting the locking peg 100 is that the extended threading, when the locking peg is advanced, will cut into the bone, whereas a traditional locking peg 30 has no such extended threading to cut into the bone. In this regard, the threading on portion 130 is preferably of a diameter greater than portion 140 so as to dig into the walls of a pilot hole created in the bone to receive the unthreaded portion 140.

Figure 4B:
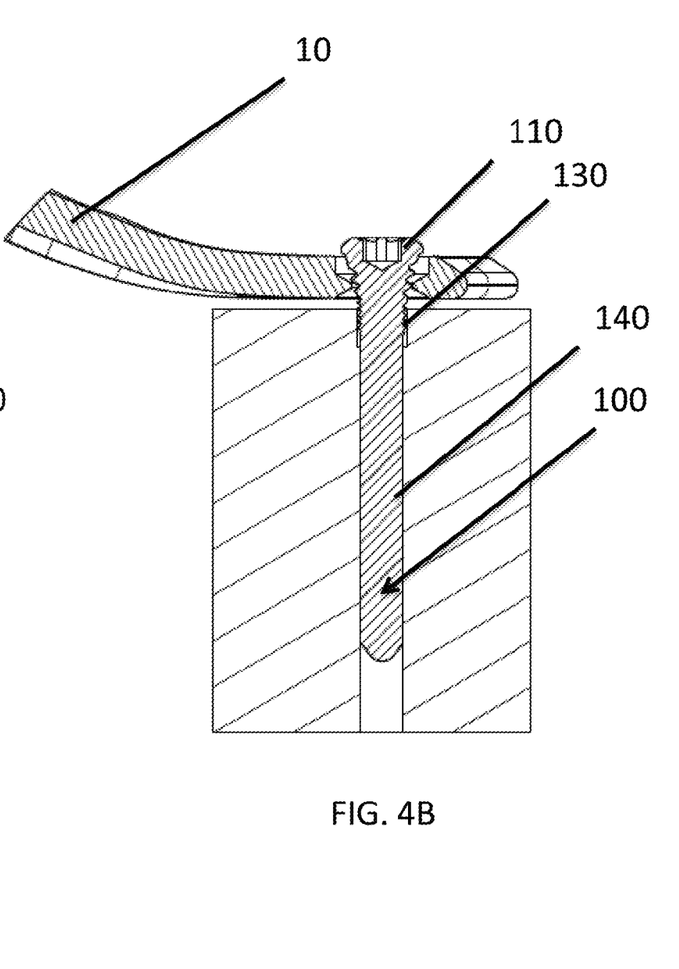
Figure 4C:
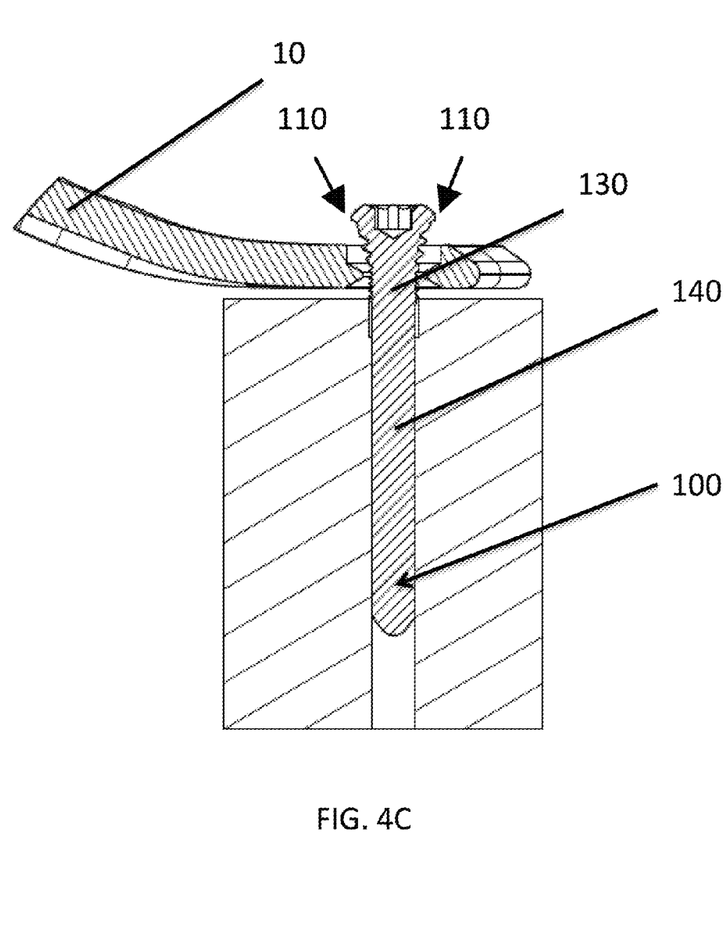

As illustrated in FIG. 4B, the locking peg 100 may be unscrewed from the bone and bone plate 10 in a fashion generally similar to a traditional locking peg 30 by rotating the locking peg 100 counterclockwise. As the locking thread of the head 110 is rotated with respect to the corresponding thread in the locking hole of the bone plate 10, the locking peg is moved upwards by the axial force provided by rotation. However, unlike a traditional locking peg 30, the locking peg 100 described herein may be rotated an additional number of revolutions, as illustrated in FIG. 4C, due to the extended threading on the proximal end 130 of the shaft 120. As counterclockwise rotation continues, the extended threading in the bone provides additional upward axial force, whereas additional rotation in a traditional locking peg 30 would simply rotate the locking peg 30 without providing additional axial force.

In one embodiment, the extended threading of locking peg 100 adds approximately three to four additional revolutions to the unscrewing process. As such, the length of the unthreaded portion of the shaft 120 is longer than the length of the threaded portion of the shaft 120. In an embodiment with a lead of approximately 0.6 mm, the additional revolutions provide between approximately 1.8 to approximately 2.4 additional millimeters of axial movement. The additional axial movement raises the head 110 of the locking peg 100 higher than would generally be expected in a traditional locking peg 30. As a result, a user, such as a surgeon, is more easily able to grasp the head 110 of the locking peg 100 with forceps or other removal devices. This mitigates the need for a surgeon to pull on the bone plate 10 or create additional incisions. Again, the values provided above are merely illustrative and may be altered while still remaining within the scope of the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A locking peg system comprising:
   a bone plate; and
   a locking peg including:
   a substantially conical threaded head at a proximal end of the locking peg and a blunt tip at the distal end of the locking peg; and
   a shaft having a substantially constant diameter extending distally from the head to a distal end of the locking peg, the shaft having a threaded proximal portion and an unthreaded distal portion with a substantially solid core, wherein a length of the unthreaded distal portion of the shaft is greater than a length of the threaded proximal portion of the shaft,
   wherein a first thread extends continuously from the head to the proximal portion of the shaft, the threaded head forming a locking thread having a first pitch, and a second thread extends between adjacent portions of the first thread only on the proximal portion of the shaft, the proximal portion of the shaft having a second pitch approximately half the first pitch;
   wherein when the locking peg is inserted through the bone plate and into a bone on which the bone plate is positioned, the threaded proximal portion of the shaft is adapted to extend beyond the bone plate and into the bone between approximately 2 and approximately 6 thread revolutions;
   wherein the blunt tip lacks a sharpened tip and is adapted to be inserted into a pilot hole in the bone without the blunt tip cutting the bone.

2. The locking peg system of claim 1, wherein the threaded proximal portion of the shaft, when the locking peg is inserted through the bone plate and into the bone on which the bone plate is positioned, is adapted to extend between approximately 3 and approximately 5 thread revolutions beyond the bone plate and into the bone.

3. The locking peg system of claim 2, wherein the threaded proximal portion of the shaft, when the locking peg is inserted through the bone plate and into the bone on which the bone plate is positioned, is adapted to extend approximately 4 thread revolutions beyond the bone plate and into the bone.

4. The locking peg system of claim 1, wherein the threaded proximal portion of the shaft has at least one cutting flute positioned at a distal end of the threaded proximal portion of the shaft.

5. The locking peg system of claim 1, wherein a diameter of the threaded proximal portion including the threads is greater than a diameter of the unthreaded distal portion.

* * * * *